US008802058B2

(12) United States Patent
Martin et al.

(10) Patent No.: US 8,802,058 B2
(45) Date of Patent: Aug. 12, 2014

(54) PHARMACEUTICAL COMPOSITIONS AND METHODS FOR ADMINISTERING THE SAME

(75) Inventors: James H. Martin, Burr Ridge, IL (US); Christopher J. Sciarra, Patterson, NY (US); John J. Sciarra, Locust Valley, NY (US)

(73) Assignee: Gelmed, LLC, Burr Ridge, IL (US)

( * ) Notice: Subject to any disclaimer, the term of this patent is extended or adjusted under 35 U.S.C. 154(b) by 328 days.

(21) Appl. No.: 13/088,653

(22) Filed: Apr. 18, 2011

(65) Prior Publication Data

US 2011/0256070 A1 Oct. 20, 2011

Related U.S. Application Data

(60) Provisional application No. 61/325,489, filed on Apr. 19, 2010.

(51) Int. Cl.
 *A61K 9/12* (2006.01)

(52) U.S. Cl.
 USPC .............................................. 424/45; 424/43

(58) Field of Classification Search
 CPC ........................... A61K 31/5513; A61K 9/124
 USPC ..................................... 424/45, 43
 See application file for complete search history.

(56) References Cited

U.S. PATENT DOCUMENTS

| | | | |
|---|---|---|---|
| 6,524,557 B1 * | 2/2003 | Backstrom et al. ............. | 424/46 |
| 7,090,830 B2 * | 8/2006 | Hale et al. ....................... | 424/45 |
| 7,128,897 B2 * | 10/2006 | Osbakken et al. .............. | 424/45 |
| 7,342,115 B2 * | 3/2008 | Hutchison et al. ............. | 546/301 |
| 7,585,493 B2 | 9/2009 | Hale et al. | |
| 2004/0247534 A1 * | 12/2004 | Stoltz .............................. | 424/52 |
| 2007/0237724 A1 | 10/2007 | Abram et al. | |
| 2008/0292560 A1 | 11/2008 | Tamarkin et al. | |

OTHER PUBLICATIONS

Schipper et al "Nasal Insulin Delivery with Dimethyl-B - Cyclodextrin as an Absorption Enhancer in Rabbits: Powder More Effective than Liquid Formulations," Pharm. Res. 10:682, 1993.*
Crowder et al., "2001: An Odyssey in Inhaler Formulation and Design," Pharmaceutical Therapy, pp. 99-113 (2001).
Melani, "Inhalatory therapy training: a priority challenge for the physician," Acta Biomed, 78(3):233-245 (2007).
International Search Report for PCT/US2011/33217, dated Sep. 9, 2011.
Written Opinion for PCT/US2011/33217, dated Sep. 9, 2011.
Extended European Search Report EP 11 79 0140 mailed Aug. 13, 2013.

* cited by examiner

*Primary Examiner* — Suzanne Ziska
(74) *Attorney, Agent, or Firm* — Hoffmann & Baron, LLP

(57) ABSTRACT

The present invention provides pharmaceutical compositions and methods for dispensing the same using an aerosol whereby the composition takes the form of foam. Additionally, the present invention provides a barrier system including a concentrate separated from a non-chlorine aerosol propellant wherein the concentrate includes a non-aqueous solvent, an emulsifying agent, a thickening agent, at least one medicament and optionally an aqueous solvent.

26 Claims, 1 Drawing Sheet

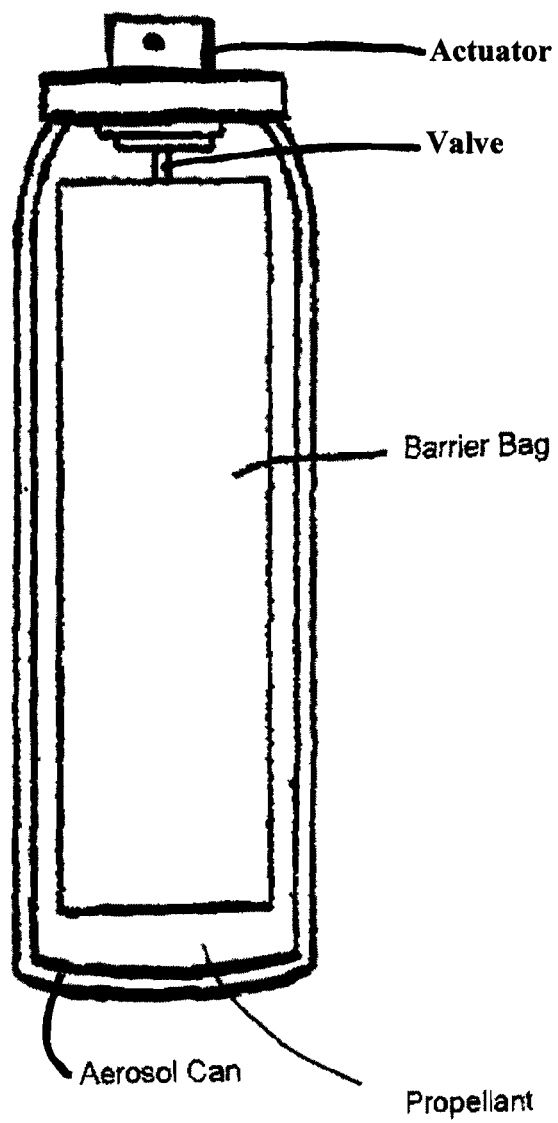

PHARMACEUTICAL COMPOSITIONS AND METHODS FOR ADMINISTERING THE SAME

CROSS-REFERENCE TO RELATED APPLICATIONS

This application claims the benefit of U.S. Provisional Application No. 61/325,489, filed Apr. 19, 2010, the content of which is incorporated herein by reference.

FIELD OF THE INVENTION

The present invention provides pharmaceutical compositions and methods for administering the same. In particular, such pharmaceutical compositions may be administered using an aerosol dispenser such that the pharmaceutical composition takes the form of foam. Additionally, provided is a barrier system including a concentrate separated from a non-chlorine aerosol propellant wherein the concentrate includes a non-aqueous solvent, an emulsifying agent, a thickening agent, at least one medicament and optionally an aqueous solvent.

BACKGROUND OF THE INVENTION

Aerosols, in commercial use since the 1950s, are commonly used to deliver therapeutic agents. Certain aerosols depend upon the power of a liquefied or compressed gas to dispense one or more medicaments from a closed system upon actuation of a valve. For example, current treatment for asthmatic patients includes medications delivered by metered dose aerosols.

Although aerosols provide a useful approach to dispensing medicaments, their effectiveness can be limited by the amount of surface area that is contacted by the medicament(s). Likewise, the effectiveness of medicaments in general, is limited by patient compliance. For example, administration of medicaments is oftentimes difficult to achieve in uncooperative or combative patients (such as in children or patients with an altered mental state) as well as those with difficulty swallowing. Thus, there is a need for improved pharmaceutical compositions that provide increased efficacy and/or foster greater patient compliance.

SUMMARY OF THE INVENTION

The present invention provides compositions including a non-aqueous solvent, a non-chlorine aerosol propellant, an emulsifying agent, a thickening agent, at least one medicament and optionally an aqueous solvent. Further, provided are methods for dispensing such compositions using an aerosol whereby the composition takes the form of foam. Additionally, the present invention provides a barrier system including a concentrate separated from a non-chlorine aerosol propellant wherein the concentrate includes a non-aqueous solvent, an emulsifying agent, a thickening agent, at least one medicament and optionally an aqueous solvent.

In one aspect, this invention dispenses the formulation from a barrier system wherein the active ingredient, foaming agent and foaming gas are separated from the propellant gas that is exerting pressure on the barrier system. The said propellant gas that is exerting pressure on the barrier system has a higher pressure than the foaming gas, thereby keeping the foaming gas in a liquid state within the formulation.

BRIEF DESCRIPTION OF THE DRAWING

FIG. 1 illustrates a barrier system suitable for use in accordance with the present invention. Notably, the barrier bag contains a concentrate therein which is separated from a propellant.

DETAILED DESCRIPTION OF THE INVENTION

As used herein the following terms shall have the definitions set forth below.

As used herein, the phrase "pressure container" refers to a closed system that has the ability to dispense a fluid under pressure upon the opening of a valve. Pressure containers include aerosol products that use propellants and non-aerosol products that rely on mechanical methods such as stretched elastomerics (see, e.g., U.S. Pat. No. 4,387,833), and pistons that compress springs.

As used herein, the phrase "barrier system" refers to a closed system that separates a product to be dispensed from a pressure source. The pressure source can be propellant gases, elastomerics (such as rubber sleeves) or pistons and springs.

As used herein, the phrase "emulsifying agent" refers to a substance that is soluble in both oil and water and that enables oil(s) to be uniformly dispersed in water as an emulsion. For example, an emulsifying agent is commonly an emulsifying wax.

As used herein, the phrase "emulsifying wax" refers to a waxy solid prepared from cetostearyl alcohol containing a polyoxyethylene derivative of a fatty acid ester of Sorbitan.

As used herein the term "medicament" refers to a pharmaceutically active agent. For example, a medicament can be absorbed or reside on the surface of a patient following administration thereof whereby it confers a biological effect. A medicament can be any pharmaceutically active agent that is known for treating and/or preventing certain medical disorders or conditions. Additionally, a medicament can be used to induce a certain condition.

As used herein, the term "thickening agent" refers to a substance which, when added to various blends of aqueous and non-aqueous solutions, increases viscosity without substantially modifying its other properties, such as taste. A thickening agent provides body, increases stability, and improves suspension of ingredients present therein.

As used herein the term "treating" means to ameliorate one or more symptoms associated with a referenced disorder or condition.

As used herein, the term "preventing" means to mitigate a symptom of a referenced disorder or condition, or confer immunity.

As used herein the phrase "an effective amount" means an amount effective to prevent and/or treat a patient at risk for developing or diagnosed with a referenced disorder or condition, thus producing the desired therapeutic effect. Additionally, "an effective amount" means an amount effective to induce a particular condition or state desired in a patient (e.g., sedation).

As used herein the term "patient" means a mammal (e.g., a human, a cat, a dog).

Methods of Preparing Compositions

Compositions of the present invention are formed by mixing to homogeneity the following ingredients: a non-aqueous solvent, a non-chlorine aerosol propellant, an emulsifying agent, a thickening agent, at least one medicament and optionally an aqueous solvent. In one embodiment, mixing is conducted at room temperature.

In certain embodiments, the ratio of concentrate (including a non-aqueous solvent, an emulsifying agent, a thickening agent, at least one medicament and optionally an aqueous solvent) to non-chlorine aerosol propellant is in the range of 98:2 to 50:50. Desirably, the ratio of concentrate to non-chlorine aerosol propellant is in the range of 95:5 to 75:25. In one embodiment, the ratio of concentrate to non-chlorine aerosol propellant is 85:15.

In one embodiment, the aqueous solvent is water.

In certain embodiments, the composition does not include added aqueous solvent.

Suitable non-aqueous solvents include, but are not limited to, an alcohol, a glycerol, a glycol (including propylene glycol) or a combination of two or more thereof.

Suitable non-chlorine aerosol propellants include, but are not limited to, P-134a (1,1,1,2-tetraflouroethane) P-227ea (1,1,1,2,3,3,3-heptaflouropropane), P-236fa (1,1,1,3,3,3-hexafluoropropane), P-245fa (1,1,1,3,3-pentaflouropropane), P-152a (1,I-diflouroethane), an atmospheric gas, or a combination of two or more thereof. For example, suitable atmospheric gases include, but are not limited to, air, nitrogen, nitrous oxide, carbon dioxide or a combination of two or more thereof. Desirably, the atmospheric gas is liquefied and/or compressed. In certain embodiments, the non-chlorine aerosol propellant is P-134a, P227ea or a combination thereof.

Suitable emulsifying agents include an emulsifying wax, a stearic acid, cetyl alcohol or a combination of two or more thereof. In one embodiment, the emulsifying agent is a combination of an emulsifying wax and a stearic acid. In one embodiment, emulsifying wax is present in a range from 0.01% to 10%. Desirably, emulsifying wax is present in a range from 0.05% to 5%. In one embodiment, cetyl alcohol is present in a range from 0.1% to 10%. Desirably, cetyl alcohol is present in a range from 0.5% to 1%. In one embodiment, Stearth-10 is present in a range from 0.01% to 10%. Desirably, Stearth-10 is present in a range from 0.05% to 5%.

Suitable thickening agents include, but are not limited to, a fatty acid, a starch, a vegetable gum, a protein, a sugar, or a combination of two or more thereof. For example, a suitable sugar is a cyclic oligosaccharide.

Suitable medicaments include those which may be ingested or applied topically to the skin, including the external auditory canal and onto mucosal areas including buccal, sublingual, nasal, conjunctival, vaginal, meatal and rectal surfaces to achieve their effect. In certain embodiments, at least one medicament is taken up systemically.

In one embodiment, at least one medicament is a narcotic blocker, an antibacterial agent, virucidal agent, a fungicidal agent, a beta-blocker, a cardiotropic, a vaso-active agent, a hormone, a decongestant, a vaccine, an analgesic or a sedative.

Exemplary analgesics include, but are not limited to, paracetamol (also known as para-acetylaminophenol and in the US as acetaminophen), non-steroidal anti-inflammatory drugs (NSAIDs) (e.g., salicylates), and opioid drugs (e.g., morphine and opium).

Exemplary sedatives include, but are not limited to, opiates, barbituates and benzodiazepines.

In one embodiment, at least one medicament is an anti-seizure agent. For example, suitable anti-seizure agents include, but are not limited to, midazolam and diazepam.

In one embodiment, at least one medicament is a narcotic blocker (e.g., naloxone) or a benzodiazepine antagonist (e.g., flumazenil).

In one embodiment, at least one medicament is a topical decongestant (e.g., oxymetazoline).

One or more additives may be added to the compositions of the present invention including, but not limited to, preservative(s), flavoring agent(s) and coloring agent(s) in an appropriate amount as is known to one skilled in the art of formulations to achieve the desired effect. For example, suitable preservatives include, but are not limited to, methyl paraben, propyl paraben, or a combination thereof.

The composition may be in the form of a liquid, foam, film, or gel. In certain embodiments, (for example, under which the composition is stored) the composition is in the form of a liquid, desirably a homogenous liquid. In certain other embodiments, (for example, following discharge thereof from an aerosol), the composition is in the form of foam. In yet other embodiments, the composition is in the form of a film or gel (for example, as may occur following drying of the foam form of the composition).

Notably, the inclusion of an aqueous solvent depends upon the nature or type of medicament(s) present within the composition and the desired properties of the foam formed therefrom as discussed, for example, with regard to intranasal administration of the composition below.

The physical and/or chemical properties of a medicament used in a composition of the present invention can be altered. For example, using cyclodextrins, the hydrophilicity of a medicament can be increased by forming a complex with cyclodextrins.

Additionally, the pH of the composition can be adjusted to minimize irritation upon administration thereof. For example, a target pH for the composition may by achieved by altering the ratio of non-aqueous solvent to aqueous solvent. In one embodiment, the pH of the composition is between pH 4 to pH 9. In certain embodiments for nasal administration, a desirable pH is 7±1.5.

Exemplary compositions of the present invention include the following ingredients: at least one medicament, an emulsifying wax, a stearic acid, propylene glycol, ethyl alcohol, methyl paraben, propyl paraben, P-I34a and optionally distilled water. In certain embodiments of the aforementioned composition, at least one medicament is selected from the group consisting of diazepam, midazolam, naloxone, and flumazenil.

Storage of Compositions

The composition of the present invention may be housed in a container with a valve and actuator for dispensing the composition in the form of an aerosol.

In certain embodiments, compositions of the present invention may be stored in a pressure container under a pressure greater than atmospheric pressure.

Alternatively, a barrier system may be employed wherein a concentrate (including a mixture having a non-aqueous solvent, an emulsifying agent, a thickening agent, at least one medicament and optionally an aqueous solvent) is separated from a non-chlorine aerosol propellant as depicted in FIG. 1. Further, the non-chlorine aerosol propellant exerts pressure on the barrier system and has a higher pressure than the concentrate.

Suitable barrier systems include, but are not limited to, the barrier bag system as described in the Special Report on Alternative Packaging Systems in the December 2005 issue of *Spray Technology & Marketing* magazine.

Notably, the storage of the composition in a barrier system provides means for maintaining the concentrate in a homogenous liquid state, ensuring consistency of the concentrate mixture and hence, more accurate dosing of medicament. This is a particular concern when employing a metered aerosol dispenser wherein multiple doses of medicament are present.

Routes of Administration

The compositions of the present invention may be administered orally or topically to the skin, including the external auditory canal and onto mucosal areas including buccal, sublingual, nasal, conjunctival, vaginal, meatal and rectal surfaces.

In one embodiment, the composition is administered orally for ingestion thereof. In one embodiment, the composition is administered intranasally. In one embodiment, the composition is administered conjunctivally.

Compositions of the present invention administered orally for ingestion or buccal absorption are particularly desirable for administration to children and in those that have swallowing difficulties as the composition takes the form of foam when administered using an aerosol.

Compositions of the present invention administered topically can act locally on or within the surface area they are applied to or can even be absorbed into the vascular circulation and act systemically. Examples include topical antibiotics which act locally on the surface, vasoconstrictors which act locally within the area they are applied to as well as agents absorbed into the circulation that act systemically. Moreover, some medicaments can act both locally and systemically, such as cocaine, which causes vasoconstriction locally and exerts cardiovascular and central nervous effects systemically.

In nasal applications there is an ability to calculate the mucosal surface area needed to be covered by the foam form of a composition of the present invention. For example, the average adult nasal mucosal surface of one nostril ranges from 75 to 90 $cm^2$. The diameter of a sphere of foam needed to cover the larger nostril surface area is about 5.35 cm. Additionally, occlusion of the nostril for a brief period of time after application of the foam may be employed to improve the coating ability on the nasal mucosa by minimizing flow into the posterior nasopharynx. In this situation, foams that degrade quickly would be desirable. Alternatively, the insertion of a soft nasal trumpet prior to intranasal administration of the composition allows for continued nasal airway flow while the foam expands and coats the nasal turbinates. In this situation, foams that slowly degrade could be utilized to prolong absorption time and also increase bioavailability of the medicament(s).

Importantly, the compositions of the present invention when administered using an aerosol take the form of foam which can expand after application thereof to coat a surface area in a manner that is not possible using conventional aerosols. In particular, foams can provide broader surface area coverage and even coat tortuous pathways (including the intranasal turbinates).

Methods of Use

Compositions of the present invention are particularly suitable for use in treating and/or preventing conditions including, but not limited to: seizures, panic attacks, infections (e.g., nasal Methicillin-resistant Staphylococcus aureus (MRSA), sinusitis, otitis externa, and cellulitis), burns, wounds, nausea, chest pain, nasal congestion, Eustachian tube dysfunction, vaginosis, vaginal inflammation, rectal inflammation and hemorrhoids. Additionally, compositions of the present invention are suitable for inducing a condition, such as, sedation.

For example, in treating and/or preventing chest pain, at least one medicament for inclusion in a composition of the present invention is nitroglycerin. Further, such composition can be administered buccally or topically to dermal or mucosal surfaces.

Dosage

The amount of effective medicament(s) for preventing or treating a referenced disorder (which the medicament is indicated for) can be determined on a case-by-case basis by those skilled in the art. The amount and frequency of administration of the medicament(s) will be regulated according to the judgment of the attending clinician (physician) considering such factors as age, condition and size of the patient as well as risk for developing such disorder or severity of the symptoms of the referenced disorder being treated.

Methods for Administering Composition

Methods for administering the compositions of the present invention to a patient in need thereof include the steps of discharging a dose of such composition from an aerosol dispenser charged with the composition wherein the aerosol dispenser has either a metering valve or a continuous valve. In certain embodiments, the aerosol dispenser includes a barrier system as described above.

A metering valve provides metered dosing of the compositions of the present invention. Alternatively, a continuous valve system can be employed whereby a one-time actuation of the valve depletes the contents contained therein providing a single dose of the composition of the present invention.

Metering valves can be fixed for a unit dose or adjusted for delivery of a varied amount of composition. Suitable metering valves and actuators are described, for example, in U.S. Pat. Nos. 4,892,232; 5,085,351; 5,105,995; 5,183,187; 5,199,616; 5,484,088; 6,695,175; 6,910,606, and 7,575,134 by Martin.

Exemplary descriptions on how to assemble and use an aerosol canister or container can be found, for example, in Chapter 50 by John Sciarra and Christopher Sciarra, in *The Science and Practice of Pharmacy*, $21^{st}$ Edition, Ed.: David B. Troy, Lippincott Williams & Wilkins, Baltimore and Philadelphia (2006).

In certain embodiments wherein the composition is discharged into a nostril of the patient for delivery to the nasal mucosa, a nasal trumpet is inserted into the nostril prior to discharge of the composition.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Preparation of Diazepam Composition

The following ingredients 0.0110 g of diazepam, 7.9860 g of propylene glycol, 1.1000 g of dehydrated alcohol, 0.1375 g of emulsifying wax, 0.0467 g of cetyl alcohol, 0.0468 g of Steareth-10, 0.0022 g of propyl paraben, 0.0198 g of methyl paraben, and 1.6500 g of P-134a were mixed at room temperature to homogeneity. Notably, the resultant composition contained 0.1% by weight diazepam.

Example 2

Bioavailability of Diazepam Compositions

In a comparative study, rats were administered either a commercially available diazepam rectal gel (Diastat®) rectally, a diazepam intravenous preparation via intravenous injection, or the composition detailed in Example 1 rectally. Notably, the composition of Example 1, upon discharge from an aerosol dispenser formed foam. The rats each received a dose of 10 mg/kg.

Each experimental group consisted of at least 5 male Sprague-Dawley rats each being 300-350 g in weight. The rats were fasted overnight for 16 hours prior to receiving a dose of diazepam. In addition, the rats were kept under anesthesia with a 1 g/kg intraperitoneal dose of 40% urethane for the duration of the study.

Blood samples were collected by the orbital sinus technique at 0, 10, 20, 30, 45, 60 and 120 minutes following administration of a dose of diazepam. The blood samples were placed into tubes containing disodium EDTA. Plasma samples were isolated from these blood samples following brief centrifugation at 3,500 rpm. The plasma samples were subsequently vortex mixed with an equal volume of an internal standard solution (carbamazepine in 0.1% $HClO_4$ in acetonitrile) and centrifuged at 6,000 rpm for 10 minutes. The resultant clear supernatants were analyzed for diazepam content by HPLC on a $C^{18}$ chromatographic column, with a methanol/acetonitrile/acetate buffer pH 4.0 (50:5:45) mobile phase at 1.2 ml/minute, and a detector set at 235 nm and 0.1 AUFS. Relevant pharmacokinetic parameters ($C_{max}$, $T_{max}$, $t_{1/2}$, $K_{el}$, $K_a$, $AUC_{0-2\,hr}$ and F values), summarized in Table 1 below, were calculated based on the level of diazepam detected in the plasma samples.

TABLE 1

Pharmacokinetic parameters of rats administered Rectal Foam, Rectal Gel or Intravenous Injection of 10 m/kg Diazepam

|  | Rectal Foam (Composition of Example 1) | Rectal Gel | Intravenous Injection |
|---|---|---|---|
| $C_{max}$ (ng/mL) | 847.1 ± 171.5 | 259.7 ± 38.2 | 2928.0 ± 228.0 |
| $T_{max}$ (min) | 45 | 20 | — |
| $T_{1/2}$ (min) | 57.3 | 40.8 | 33.0 |
| $K_{el}$ (min$^{-1}$) | 0.012 | 0.017 | 0.011 |
| $K_a$ (min$^{-1}$) | 0.039 | 0.240 | — |
| AUC (ng/mL · min) | 1000.5 | 153.3 | 2550.3 |
| F (%) | 39.2 | 6.0 | — |

As reflected by the pharmacokinetic parameters summarized in Table 1, systemic absorption of the composition of Example 1 administered rectally in the form of foam was almost immediate. In fact, the $K_a$, $T_{max}$ and $T_{1/2}$ values of the diazepam gel administered intravenously rectally (0.024 min$^{-1}$, 20 minute and 40.8 minute, respectively) were lower than those of the diazepam foam (0.039 min$^{-1}$, 45 min and 57.3 min, respectively). Further, the $C_{max}$ of the diazepam foam was about 3.25-fold higher than that of the diazepam gel (847.1 ng/ml vs. 259.7 ng/ml); with a bioavailability about 6.5-fold higher than that of the diazepam gel (F=39.2% vs. 6.0%). Thus, the diazepam foam administered rectally delivered more diazepam into the plasma and provided a more sustained plasma level of diazepam than the diazepam gel administered rectally when given at an equal dose and monitored over the same time period.

Though not meant to be limited by any theory with the subject invention, the differences in in vivo performance observed for the diazepam composition of the present invention administered rectally as foam compared to the diazepam gel administered rectally is believed to be due to the differences in formulation characteristics.

Example 3

Storage Stability of Diazepam Composition

A composition as detailed in Example 1 was prepared. The composition was packaged under pressure in a 15 ml aluminum aerosol canister fitted with a valve stem and a plastic rectal applicator. The chemical stability, in vitro release rate of the medicament from the foam form of the composition, canister pressure, and physicochemical properties of the foam produced upon discharge from the canister (i.e., appearance, delivery rate, volume, expansion ratio, liquefaction volume, density, temperature, apparent pH) were also evaluated.

The composition was found to be stable following storage for 6 months under regular storage stability test conditions of 25° C./60% RH and accelerated storage stability test conditions of 40° C./75% RH. In fact, no substantial changes in the stability of the composition were noted following storage under the aforementioned conditions.

In brief, no evidence of corrosion or pitting along the lining of the canister was detected within 6 months. Further, the medicament, diazepam, remained stable in the composition during storage within the aerosol canister for at least 6 months; and was released immediately when delivered into an aqueous dissolution medium at 37° C. Additionally, the foam form of the composition exhibited excellent physical and chemical stability. In particular, the foam generated from the composition using the aerosol was white, cohesive, uniform in appearance and smooth in texture. The pressure of the aerosol canister ranged from 43 to 51 psig following storage for a 3-month period under accelerated storage stability test conditions of 40° C./75% RH. Further, following such storage, the foam discharged yielded the following desirable physicochemical properties: delivery rate from 1.06 to 1.29 g/sec; volume from 70 to 80 mL expansion ratio from 0.98-1.15; liquefaction volume from 6.7 to 8.6 mL; density from 0.12-0.15; temperature from 20 to 23° C.; and pH from 7.19 to 7.66.

What is claimed:

1. A composition comprising a first part comprising a non-aqueous solvent, a first non-chlorine aerosol propellant, an emulsifying agent, a thickening agent, at least one medicament and optionally an aqueous solvent; and a second part comprising a second non-chlorine aerosol propellant that has a higher pressure than the first non-chlorine aerosol propellant, wherein the second non-chlorine aerosol propellant comprises 1,1,1,2-tetrafluoroethane and has a pressure of about 80 to 100 psig; wherein the first part is separated from the second part and the second part exerts pressure on the first part such that the first non-chlorine aerosol propellant is maintained as a liquid and the first part is a homogenous liquid; and wherein the first part is in the form of a liquid, foam, film or gel when exposed to atmospheric pressure.

2. The composition of claim 1, wherein the aqueous solvent is water.

3. The composition of claim 1, wherein the non-aqueous solvent is an alcohol, a glycerol, a glycol or a combination of two or more thereof.

4. The composition of claim 1, wherein the emulsifying agent is an emulsifying wax, a stearic acid, cetyl alcohol or a combination of two or more thereof.

5. The composition of claim 1, wherein the emulsifying agent is a combination of an emulsifying wax and a stearic acid.

6. The composition of claim 1, wherein the thickening agent is a fatty acid, a starch, a vegetable gum, a protein, a sugar, or a combination of two or more thereof.

7. The composition of claim 6, wherein the sugar is a cyclic oligosaccharide.

8. The composition of claim 1, wherein at least one medicament is a narcotic blocker, an antibacterial agent, virucidal agent, a fungicidal agent, a beta-blocker, a cardiotropic, a vaso-active agent, a hormone, a decongestant, a vaccine, an analgesic or a sedative.

9. The composition of claim 1, wherein at least one medicament is midazolam or diazepam.

10. The composition of claim 1, wherein at least one medicament is naloxone or flumazenil.

11. The composition of claim 1, wherein at least one medicament is oxymetazoline.

12. The composition of claim 1, further comprising one or more additives.

13. The composition of claim 1, wherein the first non-chlorine aerosol propellant is selected from the group consisting of (1,1,1,2,3,3,3-heptaflouropropane), (1,1,1,3,3,3-hexafluoropropane), (1,1,1,3,3-pentaflouropropane), (1,1-diflouroethane) and a combination thereof.

14. The composition of claim 1, wherein the second non-chlorine aerosol propellant further comprises at least one additional aerosol propellant selected from the group consisting of (1,1-diflouroethane), an atmospheric gas and a combination thereof.

15. The composition of claim 14, wherein the atmospheric gas is selected from the group consisting of air, nitrogen, nitrous oxide, carbon dioxide and a combination thereof.

16. The composition of claim 1, wherein at least one medicament is a narcotic blocker.

17. The composition of claim 16, wherein the narcotic blocker is naloxone.

18. The composition of claim 1, wherein at least one medicament is a sedative.

19. The composition of claim 18, wherein the sedative is a benzodiazepine.

20. The composition of claim 1, wherein at least one medicament is diazepam.

21. The composition of claim 1, wherein the non-aqueous solvent comprises a combination of propylene glycol and dehydrating alcohol; and the emulsifying agent comprises a combination of an emulsifying wax, cetyl alcohol and Stearth-10.

22. The composition of claim 1, wherein the composition is stable following storage for 6 months at 25° C. and 60% relative humidity.

23. The composition of claim 1, wherein the composition is stable following storage for 3 months at 40° C. and 75% relative humidity.

24. The composition of claim 1, wherein the first non-chlorine aerosol propellant is present in an amount between 15 and 50% by weight of the first part.

25. The composition of claim 1, wherein multiple doses of medicament are present.

26. The composition of claim 14, wherein the first non-chlorine aerosol propellant is selected from the group consisting of (1,1,1,2,3,3,3-heptaflouropropane), (1,1,1,3,3,3-hexafluoropropane), (1,1,1,3,3-pentaflouropropane), (1,1-diflouroethane) and a combination thereof.

* * * * *